United States Patent [19]
Fleenor et al.

[11] Patent Number: 5,843,080
[45] Date of Patent: Dec. 1, 1998

[54] BIPOLAR INSTRUMENT WITH MULTI-COATED ELECTRODES

[75] Inventors: Richard P. Fleenor, Englewood, Colo.; James D. Isaacson, Sandy, Utah

[73] Assignee: MegaDyne Medical Products, Inc., Draper, Utah

[21] Appl. No.: 729,352

[22] Filed: Oct. 16, 1996

[51] Int. Cl.⁶ ................................. A61B 17/39
[52] U.S. Cl. .............................. 606/51; 606/52
[58] Field of Search ........................ 606/57, 52

[56] References Cited

U.S. PATENT DOCUMENTS

| | | |
|---|---|---|
| Re. 29,088 | 12/1976 | Shaw . |
| 3,685,518 | 8/1972 | Beuerle et al. . |
| 3,831,607 | 8/1974 | Lindemann ............... 606/51 |
| 3,902,494 | 9/1975 | Haberlen et al. . |
| 4,016,881 | 4/1977 | Rioux et al. ............... 606/51 |
| 4,074,718 | 2/1978 | Morrison, Jr. . |
| 4,427,006 | 1/1984 | Nottke . |
| 4,492,231 | 1/1985 | Auth ........................ 606/51 |
| 4,785,807 | 11/1988 | Blanch . |
| 4,936,842 | 6/1990 | D'Amelio et al. . |
| 5,049,148 | 9/1991 | Mehl ........................ 606/52 |
| 5,196,009 | 3/1993 | Kirwan, Jr. . |
| 5,603,712 | 2/1997 | Koranda et al. ............ 606/52 |
| 5,693,052 | 12/1997 | Weaver .................... 606/51 |

FOREIGN PATENT DOCUMENTS

| | | | |
|---|---|---|---|
| 2355521 | 1/1978 | France ....................... 606/52 |
| 3447156 | 7/1988 | Germany . |

*Primary Examiner*—Lee Cohen
*Attorney, Agent, or Firm*—John L. Sigalos

[57] ABSTRACT

An improved bipolar electrosurgical instrument with multi-coated electrodes for use in performing medical procedures. The electrodes of the instrument include opposed electrically conductive working surfaces at the distal ends thereof which are coated with a thin layer of a nickel-free high chromium material. At least non-working exposed surfaces of the distal ends are coated with a coating of an insulating material so as to be electrically insulated.

8 Claims, 1 Drawing Sheet

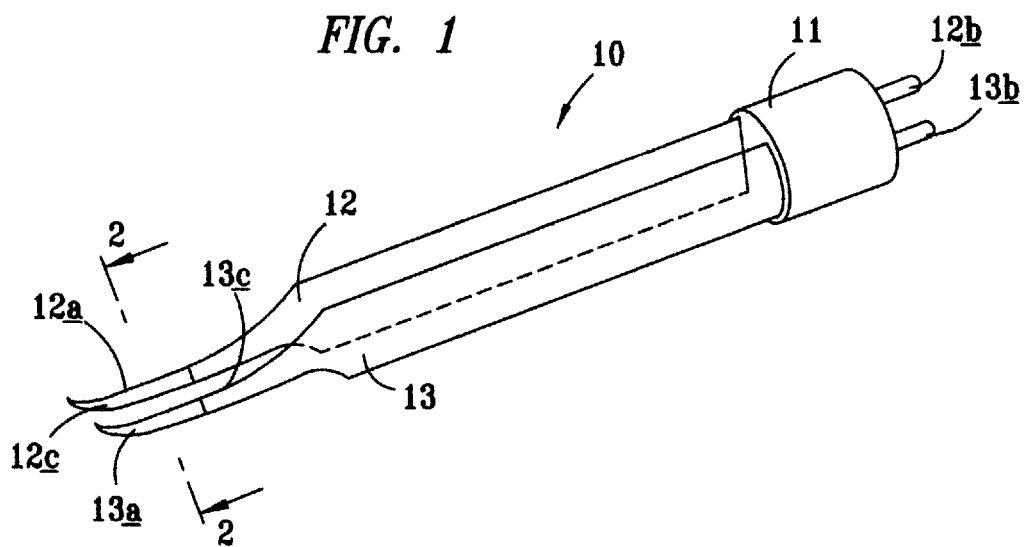
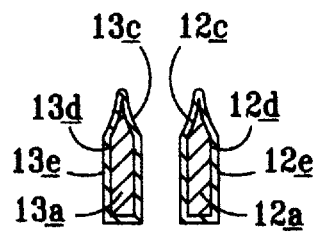
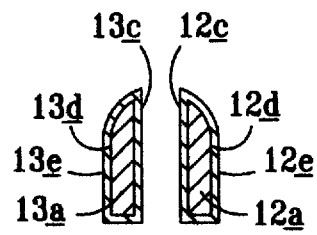
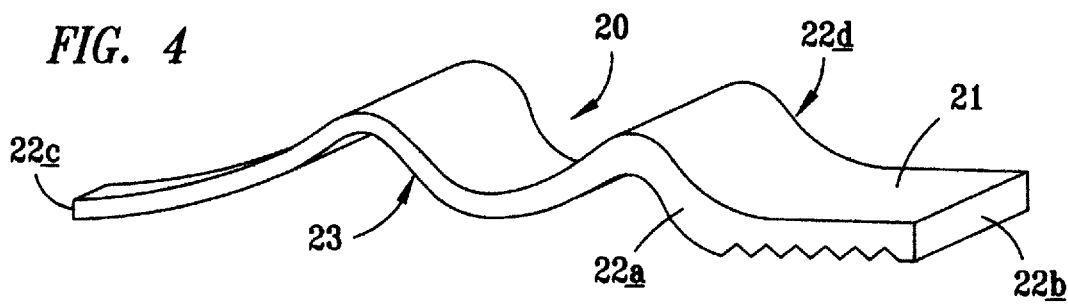

BIPOLAR INSTRUMENT WITH MULTI-COATED ELECTRODES

BACKGROUND OF THE INVENTION

The present invention relates to coated bipolar electrosurgical instruments and more particularly to such instruments that are adapted for electrosurgery at relatively high electrical current densities.

The practice of electrosurgery with bipolar electrosurgical instruments has heretofore been known, illustrative of which are the proposals set forth in co-pending U.S. patent application Ser. No. 08/523,087 filed Sep. 1, 1995, now U.S. Pat. No. 5,693,052 granted Dec. 2, 1997. the disclosure of which is specifically incorporated herein in its entirety. As set forth in that application, it was discovered that coatings having particular characteristics contributed to the effective use of the instrument for cautery purposes by reducing build-up of eschar and by facilitating the transfer of radio-frequency energy. However, it has been found that in certain applications, there is a possibility of energy transfer in areas other than those for which energy transfer is intended; and thus there has continued to be sought a further improvement to channel energy transfer through just those working surfaces for which energy transfer is intended while minimizing eschar buildup and effectively preventing or markedly reducing energy transfer elsewhere on the bipolar instrument electrode surfaces.

BRIEF SUMMARY OF THE INVENTION

The improved bipolar electrosurgical instrument according to the invention hereof includes a coating of an insulating non-conductive material, preferably a non-stick polymer such as polytetrafluoroethylene (hereinafter PTFE or TEFLON), on exposed surfaces of the regions of the electrodes other than the opposed working surfaces, the working surfaces being coated with a thin layer of a metal having at least about twice the thermal conductivity of surgical stainless steel. Preferably, the thickness of the metalized coating is in a range of thickness of about 0.0001 to about 0.0005 inches. The exact composition of the coating material may vary. However, the preferred coating material is a nickel-free high chromium composite sold under the designation ME-92 by Electrolizing Inc., 10 Houghton Street, Providence, R.I. 02904, U.S.A. It is a highly precise, non-magnetic, medically safe, USP Class VI Tripartite/ISO (International Standards Organization) certified nickel-free high chromium-composite providing a surface coating having a hardness Rc80 for stainless steels. It features a very smooth, fine molecular-grained, non-porous coating. It also has been found to transfer radio frequency electrical energy efficiently and effectively at the relatively high current densities and low voltage (less than 200 volts p—p when conducting to tissue) encountered when employing bipolar surgical techniques without any destruction of the composite coating.

OBJECTS AND FEATURES OF THE INVENTION

It is one general object of the invention to improve bipolar electrosurgical instruments.

It is yet another object of the invention to improve channeling of electrosurgical energy in such instruments.

It is another object of the invention to reduce buildup of eschar on surfaces of such instruments.

It is still another object of the invention to improve safety in use of such instruments.

In accordance with one feature of the invention, a coating having desired conductivity and non-stick characteristics is applied to working surfaces of electrosurgical instruments while an insulating coating is applied to non-working surfaces, thus channeling electrical energy and reducing energy transfer across non-working surfaces.

In accordance with another feature of the invention, the aforementioned reduction of undesired energy across non-working surfaces enhances safety of use in that it reduces undesired trauma to patent tissue.

These and other objects and features of the invention will be apparent from the following description, by way of example of a preferred embodiment, with reference to the drawing.

BRIEF DESCRIPTION OF THE DRAWING

FIG. 1 is a perspective view depicting a bipolar electrosurgical instrument having different kinds of coatings in accordance with the invention hereof;

FIG. 2 is a sectional view taken along section lines 2—2 of FIG. 1;

FIG. 3 is a sectional view illustrating planar parallel opposed working surfaces of the instrument electrodes; and FIG. 4 is a perspective view of another embodiment in which the electrodes are ribbon-shaped with lateral undulations.

DESCRIPTION OF A PREFERRED EMBODIMENT

FIG. 1 of the drawing illustrates a bipolar electrosurgical instrument 10 according to the invention having holding portion 11 from which there extend electrodes 12 and 13 each of which is coated with two different coatings as hereinafter described. At the proximal end of portion 11, there are provided a pair of electrode extensions 12b and 13b which are adapted for connection to a conventional source of electrosurgical electrical energy (not shown).

Extending at the distal extremities of electrodes 12 and 13 are end portions 12a and 13a which include inner working surfaces 12c and 13c. As is known to those skilled in the medical arts, portions 12 and 13 are made of resilient electrically conductive material that provide a spring action so that portions 12 and 13 may be moved with respect to each other to the extent desired by the using physician.

As will be observed from the drawing, the inner working surfaces 12c and 13c are opposed, that is, facing each other; and as known to those skilled in the art, they are usually planar in geometry (as illustrated in FIG. 3), although it should be understood that they may be arcuate in shape as shown in FIG. 2. Moreover, the remaining surfaces are often curved, although FIG. 4 illustrates an undulating rectangular geometry. In any event, in accordance with the principles of this invention, and in contrast with prior proposals, the inner working surfaces such as opposed surfaces 12c and 13c are coated with the aforementioned metalized coating with characteristics similar to or identical to those of ME-92, while the remaining surfaces 12d and 13d are coated with insulating materials 12e and 13e as identified above. Thus, each distal end is coated with two different coatings: the one on the inner working surface having relatively non-stick characteristics and adapted for the ready transfer of relatively high levels of electrical energy by conduction, while the remaining surfaces are entirely or partially coated with a coating that and is of a thickness to provide insulation against transmission of electrical energy from the electrodes to the patient when in use and, preferably, also has non-stick characteristics. This eliminates burning or charring of areas not intended to be cauterized. While the entirety of the non-working surfaces may be coated with the insulated coating, it will be evident that only those portions most likely to contact tissue need be so coated.

Now turning to FIG. 4, there are seen the aforementioned principles embodied in an elongated undulating ribbon-like member 20. The upper surface 21 and side edges 22a, 22b, and 22d are all covered with the aforementioned thin coating of insulating material, while the working surface 23 of the surgical side is coated with the aforementioned metalized coating with characteristics similar or identical to those of ME-92 as described above. As with electrodes 12 and 13, electrode 20 is attached to a holding portion with end 22c in contact with an electrode extension adapted for connection to a source of RF electrical energy.

It should be noted that although a part of the surgical surface 23 is shown as being serrated, such surface could as readily be made smooth and planar, depending upon the particular use in which the instrument is to be employed. It should also be noted that for sake of simplicity of description and clarity of understanding only the coated surfaces are shown in FIG. 4, the layers of coatings are generally similar to those of FIGS. 2 and 3 to which reference may be made for depiction of coating cross sections.

It will now be evident that herein there has been described improved electrosurgical instruments featuring improved characteristics of operation.

Although the inventions hereof have been described by way of preferred embodiments, it will be evident that other adaptations and modifications may be employed without departing from the spirit and scope thereof. For example, other cross sectional geometries of the electrodes could be employed.

The terms and expressions employed herein have been used as terms of description and not of limitation; and thus, there is no intent of excluding equivalents, but on the contrary it is intended to cover any and all equivalents that may be employed without departing from the spirit and scope of the invention.

We claim:

1. A bipolar eletrosurgical instrument comprising a holding portion with a pair of electrodes extending therefrom, means for individually making electrical connections to said electrodes, two different coatings covering exposed surfaces of said electrodes, one of said coatings being metalized, nickel-free and having a thickness lying within a range of from about 0.0001 to 0.0005 inches covering electrically conductive inner working surfaces at distal ends of said electrodes, and the other of said coatings being a polytetrafluoroethylene and covering only non-working surfaces of said distal ends of said electrodes and being of a thickness sufficient to electrically insulate said non-working surfaces.

2. A bipolar electrosurgical instrument according to claim 1 wherein said electrodes are essentially parallel to each other.

3. A bipolar electrosurgical instrument according to claim 1 wherein said working surfaces are essentially parallel to each other.

4. A bipolar electrosurgical instrument according to claim 1 wherein said working surfaces are opposed to each other to define opposed working surfaces.

5. A bipolar electrosurgical instrument according to claim 4 wherein said opposed surfaces are essentially planar and parallel to each other.

6. A bipolar electrosurgical instrument according to claim 1 wherein said one of said coatings is a nickel-free high chromium composite having a thickness lying within a range of from about 0.0001 to 0.0005 inches.

7. A bipolar electrosurgical instrument according to claim 1 in which said electrodes are undulating ribbon-like members.

8. A bipolar electrosurgical instrument according to claim 7 in which said undulating ribbon-like members each have serrated surfaces.

* * * * *